(12) United States Patent
Tasiemski et al.

(10) Patent No.: US 8,652,514 B2
(45) Date of Patent: Feb. 18, 2014

(54) ANTIMICROBIAL PEPTIDES

(75) Inventors: Aurélle Tasiemski, La Madeleine (FR); Michel Salzet, Bourghelles (FR); Françoise Gaill, Paris (FR)

(73) Assignees: Centre National de la Recherche Scientifique, Paris (FR); Universite des Sciences et Technologies de Lille, Villeneuve d'Ascq (FR)

( * ) Notice: Subject to any disclaimer, the term of this patent is extended or adjusted under 35 U.S.C. 154(b) by 0 days.

(21) Appl. No.: 13/518,169

(22) PCT Filed: Dec. 13, 2010

(86) PCT No.: PCT/EP2010/069536
§ 371 (c)(1),
(2), (4) Date: Sep. 12, 2012

(87) PCT Pub. No.: WO2011/076605
PCT Pub. Date: Jun. 30, 2011

(65) Prior Publication Data
US 2013/0004564 A1  Jan. 3, 2013

(30) Foreign Application Priority Data
Dec. 21, 2009  (EP) ................................ 09306289

(51) Int. Cl.
*A61K 38/17* (2006.01)
*C07K 14/435* (2006.01)
*A61K 9/48* (2006.01)
*A61P 31/04* (2006.01)
*A61P 31/10* (2006.01)
*A61P 31/12* (2006.01)

(52) U.S. Cl.
USPC ............ 424/451; 530/326; 530/350; 514/2.4; 514/3.7; 514/3.3

(58) Field of Classification Search
USPC ............ 530/326, 350; 536/23.5; 514/2.4, 3.7, 514/3.3; 435/320.1, 254.3, 252.3
IPC .................. A61K 38/17,9/48; A61P 31/04, 31/10, 31/12; C12N 15/12, 15/63, 1/15, 1/21; C07K 14/435
See application file for complete search history.

(56) References Cited

U.S. PATENT DOCUMENTS 6,642,203 B1  11/2003  Destoumieux et al.
2005/0065331 A1  3/2005  Corona villegas et al.

FOREIGN PATENT DOCUMENTS

EP         1000153 B1   10/2004
WO    2007/023163 A1    3/2007
WO    2008/066752 A2    6/2008

OTHER PUBLICATIONS

Carol L. Friedrich, Antibacterial Action of Structurally Diverse Cationic Peptides of Gram-Positive Bacteria, Antimicrobial Agents and Chemotherapy, Aug. 2000, pp. 2086-2092.*
Celine Landon, Rational design of peptides active against the gram positive bacteria *Staphylococcus aureus*, Proteins, 2008:72:229-239.*
Michel Salzet, Neuropeptide-Derived Antimicrobial Peptides from Invertebrates for Biomedical Applications, Current Medicinal Chemistry, 2005, 12, 3055-3061.*
Steven Muhle, Design of Gram-Negative Selective Antimicrobial Peptides, Biochemistry 2001, 40, 5777-5785.*
Tarquin Dorrington, Antimicrobial Peptides for Use in Oyster Aquaculture: Effect on Pathogens, Commensals, and Eukaryotic Expression systems, 2008, Journal of Shellfish Research, 27(2) pp. 365-373.*
L. Prashant, Antimicrobial peptides as an alternative to antibiotics in pigs nutrition, 2009.*
Hilde Ulvatne, Short antibacterial peptides and erythromycin act synergically against *Escherichia coli*, journal of Antimicrobial Chemotherapy, 2001, pp. 203-208.*
Madlen Mohr, Clarification of the tertiary structure of the antimicrobial peptides alvinellacin and theromacin with the help of NMR spectroscopy, Deutsche Nationalbibliothek,Order No. 1010715372 From: DissOnline [Ger. Diss.] 2010. (D0904-3), No pp. given URL: http://dnb.info11 01 0715372134; pp. 14, 26 and 44 (Figure 3) translated, enclosed.*
International Search Report, dated Apr. 20, 2011, from corresponding PCT application.
European Search Report, dated Jun. 30, 2010, from corresponding European application.

* cited by examiner

*Primary Examiner* — Julie Ha
*Assistant Examiner* — Erinne Dabkowski
(74) *Attorney, Agent, or Firm* — Young & Thompson

(57) ABSTRACT

Novel peptides having antimicrobial activity, and compositions containing the same.

10 Claims, 3 Drawing Sheets

SEQUENCE LISTING

```
<160> NUMBER OF SEQ ID NOS: 25

<210> SEQ ID NO 1
<211> LENGTH: 22
<212> TYPE: PRT
<213> ORGANISM: Artificial Sequence
<220> FEATURE:
<223> OTHER INFORMATION: peptide derived from Alvinella pompejana
<220> FEATURE:
<221> NAME/KEY: PEPTIDE
<222> LOCATION: (1)..(22)

<400> SEQUENCE: 1

Arg Gly Cys Tyr Thr Arg Cys Trp Lys Val Gly Arg Asn Gly Arg Val
1               5                   10                  15

Cys Met Arg Val Cys Thr
            20

<210> SEQ ID NO 2
<211> LENGTH: 235
<212> TYPE: PRT
<213> ORGANISM: Alvinella pompejana
<220> FEATURE:
<221> NAME/KEY: MISC_FEATURE
<222> LOCATION: (153)..(153)
<223> OTHER INFORMATION: Xaa is either L or F

<400> SEQUENCE: 2

Met Asp Cys Thr Pro Ala Pro Tyr Asp Lys Glu Gly Leu Val Thr Lys
1               5                   10                  15

Ser Gln Lys Thr Thr Met Met Ser Trp Gly Leu Met Thr Tyr Ser Val
            20                  25                  30

Val Val Thr Leu Val Leu Val Phe Leu Val Val Phe Gly Ser Leu His
            35                  40                  45

Met Glu Arg Gln Leu Gln Lys Cys Asn Ala Gln His Thr Ser Ile Glu
    50                  55                  60

Pro Leu Met Arg Glu Glu Glu Arg Phe Pro Thr Lys Val Tyr His
65                  70                  75                  80

Ile Val Asp Glu Asp Glu Ser Glu Gln Asp Ile Glu Val Asp Gln Ala
                85                  90                  95

Arg Asp Arg Glu Ile Ile His Leu Lys Glu Arg Asp Ser Asp Glu Tyr
            100                 105                 110

Ser Leu Leu Val Phe Asp Phe Lys Gln Asn Leu Gly Ala Ile Tyr Asp
        115                 120                 125

Asp Leu Thr Gly Ser Cys Tyr Val Met Gly Gly Leu Asp Ser Ser Leu
    130                 135                 140
```

```
Pro Asp Ser Val His Ile Gln Arg Xaa Leu Glu Ser Lys Thr Asp Gly
145                 150                 155                 160

Asn Asp Ile Val Lys Glu Leu Asp Tyr Thr Val Asn Ser Glu Arg Pro
                165                 170                 175

Leu Arg Asp Leu Ser Leu Ile Pro Ala Glu Leu Gln Thr Leu Cys Trp
            180                 185                 190

Gly Lys Pro Ala Phe Trp Ile Ser Lys Thr Leu Thr Glu Asp Lys Gly
        195                 200                 205

Ser His Arg Gln Lys Arg Gly Cys Tyr Thr Arg Cys Trp Lys Val Gly
        210                 215                 220

Arg Asn Gly Arg Val Cys Met Arg Val Cys Thr
225                 230                 235

<210> SEQ ID NO 3
<211> LENGTH: 169
<212> TYPE: PRT
<213> ORGANISM: Alvinella pompejana
<220> FEATURE:
<221> NAME/KEY: MISC_FEATURE
<222> LOCATION: (15)..(15)
<223> OTHER INFORMATION: Xaa is either M or I
<220> FEATURE:
<221> NAME/KEY: MISC_FEATURE
<222> LOCATION: (16)..(16)
<223> OTHER INFORMATION: Xaa is either V or W
<220> FEATURE:
<221> NAME/KEY: MISC_FEATURE
<222> LOCATION: (29)..(29)
<223> OTHER INFORMATION: Xaa is either Q or E
<220> FEATURE:
<221> NAME/KEY: MISC_FEATURE
<222> LOCATION: (60)..(60)
<223> OTHER INFORMATION: Xaa is any amino acid

<400> SEQUENCE: 3

Met Arg Glu Glu Glu Arg Phe Pro Thr Lys Val Tyr His Xaa Xaa
1               5                   10                  15

Asp Glu Asp Glu Ser Glu Gln Asp Ile Glu Val Asp Xaa Ala Arg Asp
                20                  25                  30

Arg Glu Ile Ile His Leu Lys Glu Arg Asp Ser Asp Glu Tyr Ser Leu
            35                  40                  45

Leu Val Phe Asp Phe Lys Gln Asn Leu Gly Ala Xaa Tyr Asp Asp Leu
        50                  55                  60

Thr Gly Ser Cys Tyr Val Met Gly Gly Leu Asp Ser Ser Leu Pro Asp
65                  70                  75                  80

Ser Val His Ile Gln Arg Leu Leu Glu Ser Lys Thr Asp Gly Asn Asp
            85                  90                  95

Ile Val Lys Glu Leu Asp Tyr Thr Val Asn Ser Glu Arg Pro Leu Arg
        100                 105                 110

Asp Leu Ser Leu Ile Pro Ala Glu Leu Gln Thr Leu Cys Trp Gly Lys
    115                 120                 125

Pro Ala Phe Trp Ile Ser Lys Thr Leu Thr Glu Asp Lys Gly Ser His
        130                 135                 140

Arg Gln Lys Arg Gly Cys Tyr Thr Arg Cys Trp Lys Val Gly Arg Asn
145                 150                 155                 160

Gly Arg Val Cys Met Arg Val Cys Thr
                165

<210> SEQ ID NO 4
<211> LENGTH: 99
<212> TYPE: PRT
```

```
<213> ORGANISM: Alvinella pompejana
<220> FEATURE:
<221> NAME/KEY: MISC_FEATURE
<222> LOCATION: (16)..(16)
<223> OTHER INFORMATION: Xaa is either R or Q
<220> FEATURE:
<221> NAME/KEY: MISC_FEATURE
<222> LOCATION: (17)..(17)
<223> OTHER INFORMATION: Xaa is either L or F
<220> FEATURE:
<221> NAME/KEY: MISC_FEATURE
<222> LOCATION: (20)..(20)
<223> OTHER INFORMATION: Xaa is either S or N
<220> FEATURE:
<221> NAME/KEY: MISC_FEATURE
<222> LOCATION: (24)..(24)
<223> OTHER INFORMATION: Xaa is either G or D
<220> FEATURE:
<221> NAME/KEY: MISC_FEATURE
<222> LOCATION: (60)..(60)
<223> OTHER INFORMATION: Xaa is either A or V
<220> FEATURE:
<221> NAME/KEY: MISC_FEATURE
<222> LOCATION: (73)..(73)
<223> OTHER INFORMATION: Xaa is either S or F

<400> SEQUENCE: 4

Met Gly Gly Leu Asp Ser Ser Leu Pro Asp Ser Val His Ile Gln Xaa
1               5                   10                  15

Xaa Leu Glu Xaa Lys Thr Asp Xaa Asn Asp Ile Val Lys Glu Leu Asp
            20                  25                  30

Tyr Thr Val Asn Ser Glu Arg Pro Leu Arg Asp Leu Ser Leu Ile Pro
        35                  40                  45

Ala Glu Leu Gln Thr Leu Cys Trp Gly Lys Pro Xaa Phe Trp Ile Ser
    50                  55                  60

Lys Thr Leu Thr Glu Asp Lys Gly Xaa His Arg Gln Lys Arg Gly Cys
65                  70                  75                  80

Tyr Thr Arg Cys Trp Lys Val Gly Arg Asn Gly Arg Val Cys Met Arg
                85                  90                  95

Val Cys Thr

<210> SEQ ID NO 5
<211> LENGTH: 180
<212> TYPE: PRT
<213> ORGANISM: Alvinella pompejana

<400> SEQUENCE: 5

Met Gln Arg Pro His Thr Ser Ile Glu Pro Leu Met Arg Glu Glu
1               5                   10                  15

Glu Arg Phe Pro Thr Lys Val Tyr His Ile Val Asp Asp Glu Thr
            20                  25                  30

Glu Gln Asp Ile Glu Val Asp Gln Ala Arg Asp Arg Glu Ile Ile His
        35                  40                  45

Leu Lys Glu Arg Asp Ser Asp Gly Tyr Ser Leu Leu Val Phe Asp Phe
    50                  55                  60

Lys Gln Asn Leu Gly Ala Ile Tyr Asp Asp Leu Thr Gly Ser Cys Tyr
65                  70                  75                  80

Val Met Gly Gly Leu Asp Ser Ser Leu Pro Asp Ser Val His Ile Arg
                85                  90                  95

Gln Leu Leu Glu Asn Lys Thr Asp Gly Asn Asp Ile Val Lys Glu Leu
            100                 105                 110

Asp Tyr Thr Val Asn Ser Glu Arg Pro Leu Arg Asp Leu Ser Leu Ile
        115                 120                 125
```

```
Pro Ala Glu Leu Gln Thr Leu Cys Trp Gly Lys Pro Val Phe Trp Ile
            130                 135                 140

Ser Lys Thr Leu Thr Glu Asp Lys Gly Phe His Arg Gln Lys Arg Gly
145                 150                 155                 160

Cys Tyr Thr Arg Cys Trp Thr Val Gly Arg Asn Gly Arg Val Cys Met
                165                 170                 175

Arg Val Cys Thr
            180

<210> SEQ ID NO 6
<211> LENGTH: 208
<212> TYPE: PRT
<213> ORGANISM: Artificial Sequence
<220> FEATURE:
<223> OTHER INFORMATION: peptide derived from Alvinella pompejana

<400> SEQUENCE: 6

Met Thr Tyr Ser Val Val Thr Leu Val Leu Val Phe Leu Val Val
1               5                   10                  15

Phe Gly Ser Leu His Met Glu Arg Gln Leu Gln Lys Cys Asn Ala Gln
                20                  25                  30

His Thr Ser Ile Glu Pro Leu Met Arg Glu Glu Glu Arg Phe Pro
            35                  40                  45

Thr Lys Val Tyr His Ile Val Asp Glu Asp Ser Glu Gln Asp Ile
50                  55                  60

Glu Val Asp Gln Ala Arg Asp Arg Glu Ile Ile His Leu Lys Glu Arg
65                  70                  75                  80

Asp Ser Asp Glu Tyr Ser Leu Leu Val Phe Asp Phe Lys Gln Asn Leu
                85                  90                  95

Gly Ala Ile Tyr Asp Asp Leu Thr Gly Ser Cys Tyr Val Met Gly Gly
            100                 105                 110

Leu Asp Ser Ser Leu Pro Asp Ser Val His Ile Gln Arg Leu Leu Glu
        115                 120                 125

Ser Lys Thr Asp Gly Asn Asp Ile Val Lys Glu Leu Asp Tyr Thr Val
130                 135                 140

Asn Ser Glu Arg Pro Leu Arg Asp Leu Ser Leu Ile Pro Ala Glu Leu
145                 150                 155                 160

Gln Thr Leu Cys Trp Gly Lys Pro Ala Phe Trp Ile Ser Lys Thr Leu
                165                 170                 175

Thr Glu Asp Lys Gly Ser His Arg Gln Lys Arg Gly Cys Tyr Thr Arg
            180                 185                 190

Cys Trp Lys Val Gly Arg Asn Gly Arg Val Cys Met Arg Val Cys Thr
        195                 200                 205

<210> SEQ ID NO 7
<211> LENGTH: 720
<212> TYPE: DNA
<213> ORGANISM: Artificial Sequence
<220> FEATURE:
<223> OTHER INFORMATION: nucleic acid molecule derived from Alvinella
      pompejana

<400> SEQUENCE: 7
atgacgtatt ctgtagttgt gacgctggtc ttagtgtttc ttgtcgtctt cggtagtctg    60
catatggaac ggcagctgca gaaatgcaac gcgcagcata cttcgattga accccctgatg   120 cgtgaggaag aggagcgctt tcctacaaag gtttatcaca ttgtggacga ggatgaaagc   180
gaacaagaca tcgaagtaga ccaagcacgt gaccgggaga taatccattt gaaggagcgc   240
```

| | |
|---|---|
| gatagtgatg aatattcatt acttgtcttc gatttcaagc agaatctcgg agccatttac | 300 |
| gacgatctta ccggatcgtg ttacgtcatg ggtggccttg acagcagtct gccagacagc | 360 |
| gtacatatac agcgattgct tgaaagcaag actgatggca atgacatcgt gaaggaactc | 420 |
| gactacaccg tcaactctga acgtccactg agagatctga gcctgattcc agccgagctc | 480 |
| cagacgttgt gttggggaaa acctgccttc tggatcagta agactctaac cgaagacaaa | 540 |
| ggttctcatc gtcagaagag aggttgttac acacgttgtt ggaaagttgg taggaacgga | 600 |
| cgtgtttgta tgcgtgtttg tacataactc acctgcttca tttcactgag aaacaggact | 660 |
| tattaacaat aaactaaaca ccaaatgatc tggcggctcc gtcctgccta cgcaggcaag | 720 |

<210> SEQ ID NO 8
<211> LENGTH: 763
<212> TYPE: DNA
<213> ORGANISM: Alvinella pompejana

<400> SEQUENCE: 8

| | |
|---|---|
| cttgctgaga gacaagcaga ggcaatggac tgtacgccgg caccttacga caaagaaggt | 60 |
| cttgtaacca agtcgcagaa gacgaccatg atgtcatggg gactgatgac gtattctgta | 120 |
| gttgtgacgc tggtcttagt gtttcttgtc gtcttcggta gtctgcatat ggaacggcag | 180 |
| ctgcagaaat gcaacgcgca gcatacttcg attgaacccc tgatgcgtga ggaagaggag | 240 |
| cgctttccta caaaggttta tcacattgtg gacgaggatg aaagcgaaca agacatcgaa | 300 |
| gtagaccaag cacgtgaccg ggagataatc catttgaagg agcgcgatag tgatgaatat | 360 |
| tcattacttg tcttcgattt caagcagaat ctcggagcca tttacgacga tcttaccgga | 420 |
| tcgtgttacg tcatgggtgg ccttgacagc agtctgccag acagcgtaca tatacagcga | 480 |
| ttgcttgaaa gcaagactga tggcaatgac atcgtgaagg aactcgacta caccgtcaac | 540 |
| tctgaacgtc cactgagaga tctgagcctg attccagccg agctccagac gttgtgttgg | 600 |
| ggaaaacctg ccttctggat cagtaagact ctaaccgaag acaaaggttc tcatcgtcag | 660 |
| aagagaggtt gttacacacg ttgttggaaa gttggtagga acggacgtgt ttgtatgcgt | 720 |
| gtttgtacat aactcacctg cttcatttca ctgagaaaca gga | 763 |

<210> SEQ ID NO 9
<211> LENGTH: 752
<212> TYPE: DNA
<213> ORGANISM: Alvinella pompejana

<400> SEQUENCE: 9

| | |
|---|---|
| aggcaatgga ctgtacgccg gcaccttacg acaaagaagg tcttgtaacc aagtcgcaga | 60 |
| agacgaccat gatgtcatgg ggactgatga cgtattctgt agttgtgacg ctggtcttag | 120 |
| tgtttcttgt cgtcttcggt agtctgcata tggaacggca gctgcagaaa tgcaacgcgc | 180 |
| agcatacttc gattgaaccc ctgatgcgtg aggaagagga gcgctttcct acaaaggttt | 240 |
| atcacattgt ggacgaggat gaaagcgaac aagacatcga agtagaccaa gcacgtgacc | 300 |
| gggagataat ccatttgaag gagcgcgata gtgatgaata ttcattactt gtcttcgatt | 360 |
| tcaagcagaa tctcggagcc atttacgacg atcttaccgg atcgtgttac gtcatgggtg | 420 |
| gccttgacag cagtctgcca gacagcgtac atatacagcg attgcttgaa agcaagactg | 480 |
| atggcaatga catcgtgaag gaactcgact acaccgtcaa ctctgaacgt ccactgagag | 540 |
| atctgagcct gattccagcc gagctccaga cgttgtgttg ggaaaacct gccttctgga | 600 |
| tcagtaagac tctaaccgaa gacaaaggtt ctcatcgtca gaagagaggt tgttacacac | 660 |

```
gttgttggaa agttggtagg aacggacgtg tttgtatgcg tgtttgtaca taactcacct    720
gcttcatttc actgagaaac aggacttatt aa                                  752

<210> SEQ ID NO 10
<211> LENGTH: 754
<212> TYPE: DNA
<213> ORGANISM: Alvinella pompejana

<400> SEQUENCE: 10
gcttcttgct gagagacaag cagaggcaat ggactgtacg ccggcacctt acgacaaaga    60
aggtcttgta accaagtcgc agaagacgac catgatgtca tggggactga tgacgtattc   120
tgtagttgtg acgctggtct tagtgttcct tgtcgtcttc ggtagtctgc atatggaacg   180
gcagctgcag aaatgcaacg cgcagcatac ttcgattgaa cccctgatgc gtgaggaaga   240
ggagcgcttt cctacaaagg tttatcacat tgtggacgag gatgaaagcg aacaagacat   300
cgaagtagac caagcacgtg accgggagat aatccatttg aaggagcgcg atagtgatga   360
atattcatta cttgtcttcg atttcaagca gaatctcgga gccatttacg acgatcttac   420
cggatcgtgt tacgtcatgg gtggccttga cagcagtctg ccagacagcg tacatataca   480
gcgattcctt gaaagcaaga ctgatggcaa tgacatcgtg aaggaactcg actacaccgt   540
caactctgaa cgtccactga gagatctgag cctgattcca gccgagctcc agacgttgtg   600
ttggggaaaa cctgccttct ggatcagtaa gactctaacc gaagacaaag ttctcatcg    660 tcagaagaga ggttgttaca cacgttgttg gaaagttggt aggaacggac gtgtttgtat   720
gcgtgtttgt acataactca cctgcttcat ttca                               754

<210> SEQ ID NO 11
<211> LENGTH: 815
<212> TYPE: DNA
<213> ORGANISM: Alvinella pompejana

<400> SEQUENCE: 11
tgctgagaga caagcagagg caatggactg tacgccggca ccttacgaca agaaggtct    60 tgtaaccaag tcgcagaaga cgaccatgat gtcatgggga ctgatgacgt attctgtagt   120
tgtgacgctg gtcttagtgt ttcttgtcgt cttcggtagt ctgcatatgg aacggcagct   180
gcagaaatgc aacgcgcagc atacttcgat tgaaccctg atgcgtgagg aagaggagcg   240
ctttcctaca aaggtttatc acattgtgga cgaggatgaa agcgaacaag acatcgaagt   300
agaccaagca cgtgaccggg agataatcca tttgaaggag cgcgatagtg atgaatattc   360
attacttgtc ttcgatttca agcagaatct cggagccatt tacgacgatc ttaccggatc   420
gtgttacgtc atgggtggcc ttgacagcag tctgccagac agcgtacata tacagcgatt   480
gcttgaaagc aagactgatg gcaatgacat cgtgaaggaa ctcgactaca ccgtcaactc   540
tgaacgtcca ctgagagatc tgagcctgat tccagccgag ctccagacgt tgtgttgggg   600
aaaacctgcc ttctggatca gtaagactct aaccgaagac aaaggttctc atcgtcagaa   660
gagaggttgt tacacacgtt gttggaaagt tggtaggaac ggacgtgttt gtatgcgtgt   720
ttgtacataa ctcacctgct tcatttcact gagaaacagg acttattaac ataaactaaa   780
caccaaatga tctggcgggct ccgtcctgcc tacgc                              815

<210> SEQ ID NO 12
<211> LENGTH: 782
<212> TYPE: DNA
<213> ORGANISM: Alvinella pompejana
```

-continued

<400> SEQUENCE: 12

```
gagaagcttc ttgctgagag acaagcagag gcaatggact gtacgccggc accttacgac      60
aaagaaggtc ttgtaaccaa gtcgcagaag acgaccatga tgtcatgggg actgatgacg     120
tattctgtag ttgtgacgct ggtcttagtg tttcttgtcg tcttcggtag tctgcatatg     180
gaacggcagc tgcagaaatg caacgcgcag catacttcga ttgaacccct gatgcgtgag     240
gaagaggagc gctttcctac aaaggtttat cacattgtgg acgaggatga aagcgaacaa     300
gacatcgaag tagaccaagc acgtgaccgg gagataatcc atttgaagga gcgcgatagt     360
gatgaatatt cattacttgt cttcgatttc aagcagaatc tcggagccat ttacgacgat     420
cttaccggat cgtgttacgt catgggtggc cttgacagca gtctgccaga cagcgtacat     480
atacagcgat tgcttgaaag caagactgat ggcaatgaca tcgtgaagga actcgactac     540
accgtcaact ctgaacgtcc actgagagat ctgagcctga ttccagccga gctccagacg     600
ttgtgttggg gaaaacctgc cttctggatc agtaagactc taaccgaaga caaaggttct     660
catcgtcaga agagaggttg ttacacacgt tgttggaaag ttggtaggaa cggacgtgtt     720
tgtatgcgtg tttgtacata actcacctgc ttcatttcac tgagaaacag gacttattaa     780
ca                                                                     782
```

<210> SEQ ID NO 13
<211> LENGTH: 770
<212> TYPE: DNA
<213> ORGANISM: Alvinella pompejana
<220> FEATURE:
<221> NAME/KEY: misc_feature
<222> LOCATION: (182)..(182)
<223> OTHER INFORMATION: n is a, c, g, or t

<400> SEQUENCE: 13

```
tgatgcgtga ggaagaggag cgcttcccta caaaggttta tcacatgtgg gacgaggatg      60
aaagcgaaca agacatcgaa gtagaccaag cacgtgaccg ggagataatc catttgaagg     120
agcgcgatag tgatgaatat tcattacttg tcttcgattt caagcagaat ctcggagcca     180
tntacgacga tcttaccgga tcgtgttacg tcatgggtgg ccttgacagc agtctgccag     240
acagcgtaca tatacagcga ttgcttgaaa gcaagactga tggcaatgac atcgtgaagg     300
aactcgacta caccgtcaac tctgaacgtc cactgagaga tctgagcctg attccagccg     360
agctccagac gttgtgttgg ggaaaacctg ccttctggat cagtaagact ctaaccgaag     420
acaaaggttc tcatcgtcag aagagaggtt gttacacacg ttgttggaaa gttggtagga     480
acggacgtgt ttgtatgcgt gtttgtacat aactcacctg cttcatttca ctgagaaaca     540
ggacttatta acataaacta aacaccaaat gatctggcgg ctccgtcctg cctacgcagg     600
caaggcgaag tttctgtcta tatacgcgca cgattctcat cgatcttatc gccttgtgat     660
gatgatgatc atcatcatcc agtgtacaac ctcaaagcca taacgtcaga atattaagta     720
gcatttgtag gcttttcttt ctaataaaat catgatagtc cccaaaaaaa                 770
```

<210> SEQ ID NO 14
<211> LENGTH: 770
<212> TYPE: DNA
<213> ORGANISM: Alvinella pompejana

<400> SEQUENCE: 14

```
atgcgtgagg aagaggagcg ctttcctaca aaggtttatc acattgtgga cgaggatgaa      60
agcgaacaag acatcgaagt agaccaagca cgtgaccggg agataatcca tttgaaggag     120
```

| | | | | |
|---|---|---|---|---|
| cgcgatagtg | atgaatattc | attacttgtc | ttcgatttca | agcagaatct cggagccatt | 180 |
| tacgacgatc | ttaccggatc | gtgttacgtc | atgggtggcc | ttgacagcag tctgccagac | 240 |
| agcgtacata | tacagcgatt | gcttgaaagc | aagactgatg | gcaatgacat cgtgaaggaa | 300 |
| ctcgactaca | ccgtcaactc | tgaacgtcca | ctgagagatc | tgagcctgat tccagccgag | 360 |
| ctccagacgt | tgtgttgggg | aaaacctgcc | ttctggatca | gtaagactct aaccgaagac | 420 |
| aaaggttctc | atcgtcagaa | gagaggttgt | tacacacgtt | gttggaaagt tggtaggaac | 480 |
| ggacgtgttt | gtatgcgtgt | ttgtacataa | ctcacctgct | tcatttcact gagaaacagg | 540 |
| acttattaac | ataaactaaa | caccaaatga | tctggcggct | ccgtcctgcc tacgcaggca | 600 |
| aggcgaagtt | tctgtctata | tacgcgcacg | attctcatcg | atcttatcgc cttgtgatga | 660 |
| tgatgatcat | catcatccag | tgtacaacct | caaagccata | acgtcagaat attaagtagc | 720 |
| atttgtaggc | ttttctttct | aataaaatca | tgatagtttc | ctgaaaaaaa | 770 |

<210> SEQ ID NO 15
<211> LENGTH: 757
<212> TYPE: DNA
<213> ORGANISM: Alvinella pompejana

<400> SEQUENCE: 15

| | | | | |
|---|---|---|---|---|
| gcaacgcgca | gcatacttcg | attgaacccc | tgatgcgtga | ggaagaggag cgctttccta | 60 |
| caaaggttta | tcacattgtg | gacgaggatg | aaagcgaaca | agacatcgaa gtagacgagg | 120 |
| cacgtgaccg | ggagataatc | catttgaagg | agcgcgatag | tgatgaatat tcattacttg | 180 |
| tcttcgattt | caagcagaat | ctcggagcca | tttacgacga | tcttaccgga tcgtgttacg | 240 |
| tcatgggtgg | ccttgacagc | agtctgccag | acagcgtaca | tatacagcga ttgcttgaaa | 300 |
| gcaagactga | tggcaatgac | atcgtgaagg | aactcgacta | caccgtcaac tctgaacgtc | 360 |
| cactgagaga | tctgagcctg | attccagccg | agctccagac | gttgtgttgg ggaaaacctg | 420 |
| ccttctggat | cagtaagact | ctaaccgaag | acaaaggttc | tcatcgtcag aagagaggtt | 480 |
| gttacacacg | ttgttggaaa | gttggtagga | acggacgtgt | ttgtatgcgt gtttgtacat | 540 |
| aactcacctg | cttcatttca | ctgagaaaca | ggacttatta | acataaacta acaccaaat | 600 |
| gatctggcgg | ctccgtcctg | cctacgcagg | caaggcgaag | tttctgtcta tacgcgca | 660 |
| cgattctcat | cgatcttatc | gccttgtgat | gatgatgatc | atcatcatcc agtgtacaac | 720 |
| ctcaaagcca | taacgtctag | aatattaagt | agcattt | | 757 |

<210> SEQ ID NO 16
<211> LENGTH: 730
<212> TYPE: DNA
<213> ORGANISM: Alvinella pompejana
<220> FEATURE:
<221> NAME/KEY: misc_feature
<222> LOCATION: (142)..(142)
<223> OTHER INFORMATION: n is a, c, g, or t

<400> SEQUENCE: 16

| | | | | |
|---|---|---|---|---|
| tcacattgtg | gacgaggatg | aaagcgaaca | agacatcgaa | gtagaccaag cacgtgaccg | 60 |
| ggagataatc | catttgaagg | agcgcgatag | tgatgaatat | tcattacttg tcttcgattt | 120 |
| caagcagaat | ctcggagcca | tntacgacga | tcttaccgga | tcgtgttacg tcatgggtgg | 180 |
| ccttgacagc | agtctgccag | acagcgtaca | tatacagcga | ttgcttgaaa gcaagactga | 240 |
| tggcaatgac | atcgtgaagg | aactcgacta | caccgtcaac | tctgaacgtc cactgagaga | 300 |
| tctgagcctg | attccagccg | agctccagac | gttgtgttgg | ggaaaacctg ccttctggat | 360 |

| | |
|---|---|
| cagtaagact ctaaccgaag acaaaggttc tcatcgtcag aagagaggtt gttacacacg | 420 |
| ttgttggaaa gttggtagga acggacgtgt ttgtatgcgt gtttgtacat aactcacctg | 480 |
| cttcatttca ctgagaaaca ggacttatta acataaacta aacaccaaat gatctggcgg | 540 |
| ctccgtcctg cctacgcagg caaggcgaag tttctgtcta tatacgcgca cgattctcat | 600 |
| cgatcttatc gccttgtgat gatgatgatc atcatcatcc agtgtacaac ctcaaagcca | 660 |
| taacgtcaga atattaagta gcatttgtag cttttctttt ctaataaaat catgatagtt | 720 |
| tccaaaaaaa | 730 |

<210> SEQ ID NO 17
<211> LENGTH: 652
<212> TYPE: DNA
<213> ORGANISM: Alvinella pompejana

<400> SEQUENCE: 17

| | |
|---|---|
| ggagcgcgat agtgatgaat attcattact tgtcttcgat ttcaagcaga atctcggagc | 60 |
| catttacgac gatcttaccg gatcgtgtta cgtcatgggt ggccttgaca gcagtctgcc | 120 |
| agacagcgta catatacagc gattgcttga aagcaagact gatggcaatg acatcgtgaa | 180 |
| ggaactcgac tacaccgtca actctgaacg tccactgaga gatctgagcc tgattccagc | 240 |
| cgagctccag acgttgtgtt ggggaaaacc tgccttctgg atcagtaaga ctctaaccga | 300 |
| agacaaaggt tctcatcgtc agaagagagg ttgttacaca cgttgttgga aagttggtag | 360 |
| gaacggacgt gtttgtatgc gtgtttgtac ataactcacc tgcttcattt cactgagaaa | 420 |
| caggacttat taacataaac taaacaccaa atgatctggc ggctccgtcc tgcctacgca | 480 |
| ggcaaggcga gtttctgtc tatatacgcg cacgattctc atcgatctta tcgccttgtg | 540 |
| atgatgatga tcatcatcat ccagtgtaca acctcaaagc cataacgtca gaatattaag | 600 |
| tagcatttgt aggcttttct ttctaataaa atcatgatag tttccaaaaa aa | 652 |

<210> SEQ ID NO 18
<211> LENGTH: 602
<212> TYPE: DNA
<213> ORGANISM: Alvinella pompejana

<400> SEQUENCE: 18

| | |
|---|---|
| gccatttacg acgatcttac cggatcgtgt tacgtcatgg gtggccttga cagcagtctg | 60 |
| ccagacagcg tacatataca gcgattgctt gaaagcaaga ctgatggcaa tgacatcgtg | 120 |
| aaggaactcg actacaccgt caactctgaa cgtccactga gagatctgag cctgattcca | 180 |
| gccgagctcc agacgttgtg ttggggaaaa cctgccttct ggatcagtaa gactctaacc | 240 |
| gaagacaaag gttctcatcg tcagaagaga ggttgttaca cacgttgttg gaaagttggt | 300 |
| aggaacggac gtgtttgtat gcgtgtttgt acataactca cctgcttcat ttcactgaga | 360 |
| aacaggactt attaacataa actaaacacc aaatgatctg gcggctccgt cctgcctacg | 420 |
| caggcaaggc gaagtttctg tctatatacg cgcacgattc tcatcgatct tatcgccttg | 480 |
| tgatgatgat gatcatcatc atccagtgta caacctcaaa gccataacgt ctagaatatt | 540 |
| aagtagcatt tgtaggcttt tctttctaat aaaatcatga tagtttccaa gccttaaaaa | 600 |
| aa | 602 |

<210> SEQ ID NO 19
<211> LENGTH: 715
<212> TYPE: DNA
<213> ORGANISM: Alvinella pompejana

<400> SEQUENCE: 19

```
ggaaagcgaa caagacatcg aagtagacca agcacgtgac cgggagataa tccatttgaa      60
ggagcgcgat agtgatgaat attcattact tgtcttcgat ttcaagcaga atctcggagc     120
catttacgac gatcttaccg gatcgtgtta cgtcatgggt ggccttgaca gcagtctgcc     180
agacagcgta catatacagc gattccttga agcaagact  gatggcaatg acatcgtgaa     240
ggaactcgac tacaccgtca actctgaacg tccactgaga gatctgagcc tgattccagc     300
cgagctccag acgttgtgtt ggggaaaacc tgccttctgg atcagtaaga ctctaaccga     360
agacaaaggt tctcatcgtc agaagagagg ttgttacaca cgttgttgga agttggtag      420
gaacggacgt gtttgtatgc gtgtttgtac ataactcacc tgcttcattt cactgagaaa     480
caggacttat aacataaac  taaacaccaa atgatctggc ggctccgtcc tgcctacgca     540
ggcaaggcga agtttctgtc tatatacgcg cacgattctc atcgatctta tcgccttgtg     600
atgatgatga tcatcatcat ccagtgtaca acctcaaagc cataacgtca gaatattaag     660
tagcatttgt aggcttttct ttctaataaa atcatgatag tttcccctaa aaaaa          715
```

<210> SEQ ID NO 20
<211> LENGTH: 709
<212> TYPE: DNA
<213> ORGANISM: Alvinella pompejana
<220> FEATURE:
<221> NAME/KEY: misc_feature
<222> LOCATION: (62)..(62)
<223> OTHER INFORMATION: n is a, c, g, or t

<400> SEQUENCE: 20

```
agacgatgaa accgaacaag acatcgaagt agacgaggca cgtgaccggg agataatcca      60
tntgaaggag cgcgatagtg atgaatattc attacttgtc ttcgatttca agcagaatct     120
cggagccatt tacgacgatc ttaccggatc gtgttacgtc atgggtggcc ttgacagcag     180
tctgccagac agcgtacata tacagcgatt gcttgaaagc aagactgatg acaatgacat     240
cgtgaaggaa ctcgattaca ccgtcaactc tgaacgtcca ctgagagatc tgagcctgat     300
tccagccgag ctccagacgt tgtgttgggg aaagcctgtc ttctggatca gtaagactct     360
aaccgaagac aaaggttctc atcgtcagaa gagaggttgt tacacacgtt gttggaaagt     420
tggtaggaac ggacgtgttt gtatgcgtgt ttgtacataa ctcacctgct tcatttcact     480
gagaaacagg acttattaac ataaactaaa caccaaatga tctggcggct ccgtcctagc     540
cttccccagc aaggcgaagt tcctgtctat atacgcgcac ggttctcatc gatcttatcg     600
ccttgtgatg atgatgatcc agtgaacaac ctcaaagcca tagtctagaa tattaagtag     660
catttgtagg ctttctttc taataaaatc gtaatagttt ccaaaaaaa                  709
```

<210> SEQ ID NO 21
<211> LENGTH: 754
<212> TYPE: DNA
<213> ORGANISM: Alvinella pompejana
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (143)..(143)
<223> OTHER INFORMATION: n is a, c, g, or t
<220> FEATURE:
<221> NAME/KEY: misc_feature
<222> LOCATION: (166)..(166)
<223> OTHER INFORMATION: n is a, c, g, or t

<400> SEQUENCE: 21

```
ggagcgcttt ctacaaaagg tttatcacat tgtggacgat gatgaaacga acanagacat      60
cgaagtagac caagcacgtg accgggagat aatccatttg aaggagcgcg atagtgatga     120
atattcatta cttgtcttcg atntcaagca gaatctcgga gccatntacg acgatcttac    180
cggatcgtgt tacgtcatgg gtggccttga cagtagtttg ccagacagtg tacatataca    240
gcaattgctt gaaaacaaga ctgatggcaa tgacatcgtg aaggaactcg attacaccgt    300
caactctgaa cgtccactga gagatctgag cctgattcca gccgagctcc agacgttgtg    360
ttggggaaag cctgtcttct ggatcagtaa gactctaacc gaagacaaag gttttcatcg    420
tcagaagaga ggttgttaca cacgttgttg aaagttggt aggaacggac gtgtttgtat     480
gcgtgtttgt acataactca cctgcttcat ttcactgaga acaggactt  attaacataa    540
actaaacacc aaatgatctg gcggctccgt cctgcctacg caggcaaggc gaagttcctg    600
tctatatacg cgcacgattc tcatcgatct tatcgccttg tgatgatgat gatcatcatc    660
atccagtgta caacctcaaa gccataacgt cagaatatta gtagcatttg taggctttt     720
ctttctaata aaatcgtgat agtttccaaa aaaa                                754
```

<210> SEQ ID NO 22
<211> LENGTH: 761
<212> TYPE: DNA
<213> ORGANISM: Alvinella pompejana

<400> SEQUENCE: 22

```
aaggagcgct ttcctacaaa ggtttatcac attgtggacg atgatgaaac cgaacaagac     60
atcgaagtag accaagcacg tgaccgggag ataatccatt cgaaggagcg cgatagtgat    120
gaatattcat tacttgtctt cgatttcaag cagaatctcg gagccattta cgacgatctt    180
accggatcgt gttacgtcat gggtggcctt gacagtagtt tgccagacag tgtacatata    240
cagcaattgc ttgaaaacaa gactgatggc aatgacatcg tgaaggaact cgattacacc    300
gtcaactctg aacgtccact gagagatctg agcctgattc agccgagct  ccagacgttg    360
tgttggggaa agcctgtctt ctggatcagt aagactctaa ccgaagacaa aggttttcat    420
cgtcagaaga gaggttgtta cacacgttgt tggaaagttg gtaggaacgg acgtgtttgt    480
atgcgtgttt gtacataact cacctgcttc atttcactga gaaacaggac ttattaacat    540
aaactaaaca ccaaatgatc tggcggctcc gtcctgccta cgcaggcaag gcgaagttcc    600
tgtctatata cgcgcacgat tctcatcgat cttatcgcct tgtgatgatg atgatcatca    660
tcatccagtg tacaacctca aagccataac gtcagaatat taagtagcat ttgtaggctt    720
ttctttctaa taaaatcgtg atagtttccg ggctaaaaaa a                        761
```

<210> SEQ ID NO 23
<211> LENGTH: 743
<212> TYPE: DNA
<213> ORGANISM: Alvinella pompejana

<400> SEQUENCE: 23

```
aaggtttatc acattgtgga cgatgatgaa accgaacaag acatcgaagt agaccaagca     60
cgtgaccggg agataatcca tttgaaggag cgcgatagtg atgaatattc attacttgtc    120
ttcgatttca agcagaatct cggagccatt tacgacgatc ttaccggatc gtgttacgtc    180
atgggtggcc ttgacagtag tttgccagac agtgtacata tacagcaatt gcttgaaaac    240
aagactgatg gcaatgacat cgtgaaggaa ctcgattaca ccgtcaactc tgaacgtcca    300
```

```
ctgagagatc tgagcctgat tccagccgag ctccagacgt tgtgttgggg aaagcctgtc     360
ttctggatca gtaagactct aaccgaagac aaaggttttc atcgtcagaa gagaggttgt     420
tacacacgtt gttggaaagt tggtaggaac ggacgtgttt gtatgcgtgt ttgtacataa     480
ctcacctgct tcatttcact gagaaacagg acttattaac ataaactaaa caccaaatga     540
tctggcggct ccgtcctgcc tacgcaggca aggcgaagtt cctgtctata tacgcgcacg     600
attctcatcg atcttatcgc cttgtgatga tgatgatcat catcatccag tgtacaacct     660
caaagccata acgtcagaat attaagtagc atttgtaggc ttttctttct aataaaatcg     720
tgatagtttc cgggctaaaa aaa                                             743

<210> SEQ ID NO 24
<211> LENGTH: 704
<212> TYPE: DNA
<213> ORGANISM: Alvinella pompejana
<220> FEATURE:
<221> NAME/KEY: misc_feature
<222> LOCATION: (112)..(112)
<223> OTHER INFORMATION: n is a, c, g, or t

<400> SEQUENCE: 24
gacatcgaag tagacgaggc acgtgacccg ggagataatc catttgaagg agcgcgatag      60
tgatgaatat tcattacttg tcttcgattt caagcagaat ctcggagcca tntacgacga     120
tcttaccgga tcgtgttacg tcatgggtgg ccttgacagc agtctgccag acagcgtaca     180
tatacagcga ttgcttgaaa gcaagactga tggcaatgac atcgtgaagg aactcgacta     240
caccgtcaac tctgaacgtc cactgagaga tctgagcctg attccagccg agctccagac     300
gttgtgttgg ggaaaacctg ccttctggat cagtaagact ctaaccgaag acaaaggttc     360
tcatcgtcag aagagaggtt gttacacacg ttgttggaaa gttggtagga acggacgtgt     420
ttgtatgcgt gtttgtacat aactcacctg cttcatttca ctgagaaaca ggacttatta     480
acataaacta aacaccaaat gatctggcgg ctccgtcctg cctacgcagg caaggcgaag     540
tttctgtcta tacgcgcaca cgattctcat cgatcttatc gccttgtgat gatgatgatc     600
atcatcatcc agtgtacaac ctcaaagcca taacgtctag aatattaagt agcatttgta     660
ggcttttctt tctaataaaa tcatgatagt ttccgctaaa aaaa                      704

<210> SEQ ID NO 25
<211> LENGTH: 776
<212> TYPE: DNA
<213> ORGANISM: Alvinella pompejana
<220> FEATURE:
<221> NAME/KEY: misc_feature
<222> LOCATION: (4)..(4)
<223> OTHER INFORMATION: n is a, c, g, or t

<400> SEQUENCE: 25
agtntatgtt aataagtcca gtttctcagt gaaatgaagc aggtgagtta tgtacaaaca      60
cgcatacaaa cacgtccgtt cctaccaact gtccaacaac gtgtgtaaca acctctcttc     120
tgacgatgaa aacctttgtc ttcggttaga gtcttactga tccagaagac aggctttccc     180
caacacaacg tttggagctc ggctggaatc aggctcagat ctctcagtgg acgttcagag     240
ttgacggtgt aatcgagttc cttcacgatg tcattgccat cagtcttgtt ttcaagcaat     300
tgccgtatat gtacactgtc tggcaaacta ctgtcaaggc cacccatgac gtaacacgat     360
ccggtaagat cgtcgtaaat ggctccgaga ttctgcttga aatcgaagac aagtaatgaa     420
tattcatcac tatcgcgctc cttcaaatgg attatctccc ggtcacgtgc ttggtctact     480
```

```
tcgatgtctt gttcggtttc atcatcgtcc acaatgtgat aaacctttgt aggaaagcgc    540
tcctcttctt cacgcatcag gggttcaatc gaagtatgcg ggcgttgcat ttctgcagct    600
gccgttccat atgcagacta ccgaagacga caagaaacac taggaccagc gtcacaacta    660
cagaatacgt catcagtccc catgacatca tggtcgtctt ctgcgacttg gttacaagac    720
cttctttgtc gtaaggtgcc ggcgtacagt ccattgcctc tgcttgtctc tcagca        776
```

ANTIMICROBIAL PEPTIDES

Figure 1:
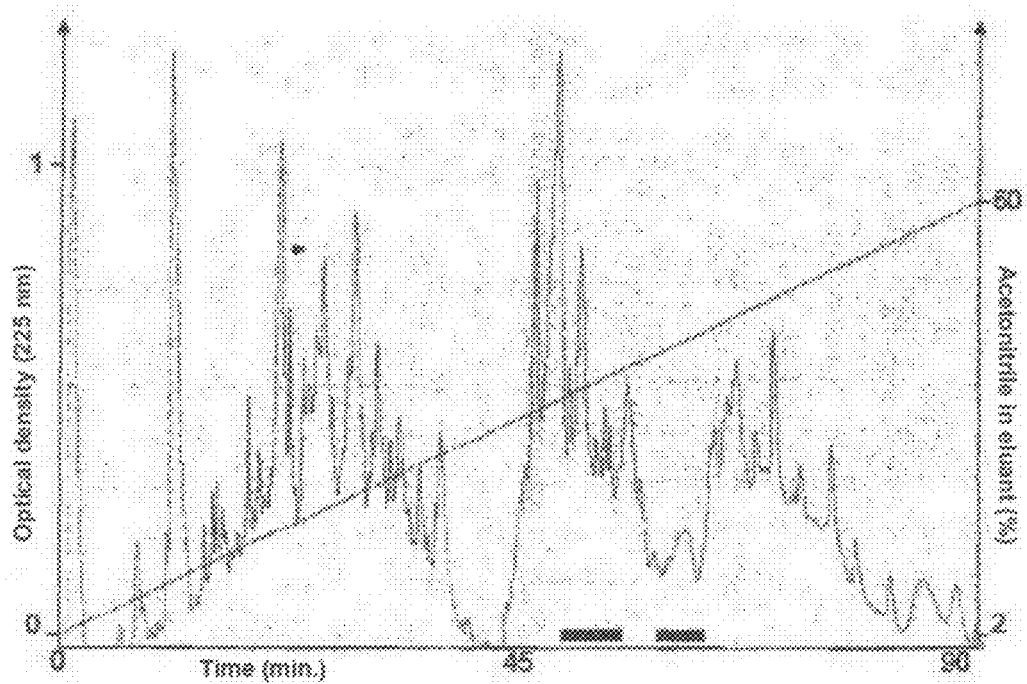

The present invention relates to novel antimicrobial peptides, their derivatives, and compositions containing the same.

Several antimicrobial peptides or derivatives are currently in advanced clinical development, essentially in the form of topical drugs (Andrès, E., Dimarcq, J. -L. Cationic anti-microbial peptides: from innate immunity study to drug development. *La revue de medicine interne* (2004), 25, 629-635). However, very few of these molecules are suggested for intended use in aquaculture, e.g. penaeidins isolated from penaeid prawns (*Penaeus vannamei*). See, EP1000153.

This can be explained by the fact that several of these antimicrobial peptides (AMPs) are inhibited in the presence of salts, which is not the case of the peptides of the present invention, inasmuch as it was isolated from a deep-sea worm: *Alvinella pompejana* or the Pompeii worm.

This worm is also considered to be the one of the most heat-tolerant organisms known to science. In fact, it resists to temperatures from 10 to 80° C., which suggests that the molecules originated from this worm such as the peptide according to the present invention, are heat-stable and thus interesting in pharmacology.

The intensification of aquaculture productions has been made possible by the important use of antibiotics. Despite constraining legislations, the preventive intended use of antibiotics is widespread, in particular during the critical phases (e.g. early stage of life, metamorphosis, animal transfer), but also during animal growth. This massive use of antibiotics tends to promote the emergent evolution of antibiotic-resistant strains, which could decimate animal husbandry. Multi-antibiotic-resistant (MAR) strains appeared in the middle of the 80's. In addition to what hardly any new antibiotic families have been discovered during the last thirty years, offering too little new products against resistant strains.

An alternative solution would be to use AMPs. These molecules, which are naturally produced by animals and plants, have a broad-spectrum and fast antibiotic activity against Gram-Negative and Gram-Positive bacteria, fungi, and enveloped viruses. Moreover, these AMPs are not immunogenic and their action on the bacterial membrane would not favour the emergent evolution of antibiotic-resistant strains. The first AMP, developed in the 90's, is a derivative of the Magainin: the Pexiganan from Magainin Pharmaceuticals, Inc. In a phase III study, the Pexiganan was included in a cream, and showed the same effectiveness as an oral antibiotic therapy with Ofloxacin, for the treatment of superinfected cutaneous ulcerations amongst diabetics. Amongst the other AMPs in development, which may be of interest for the clinician in the near future, it should be mentioned Iseganan, developed by Intrabiotics Pharmaceuticals Inc., MBI peptides developed by Micrologix Biotech Inc., and derivative peptides of Histatin developed by Periondotix Inc. (Andres et al. previously cited). But also the above-mentioned penaeidins, which seem to have a greater molecular mass in comparison with the claimed peptide isolated from *Alvinella pompejana*.

The peptides according to the invention could permit to diminish the use of antibiotics in aquaculture, by replacing a part of the latter. Due to the harmlessness of AMPs, their use would benefit brand image, but also health of the animals to be treated, customers and the environment, with no fear to favour the emergent evolution of antibiotic-resistant strains.

Thus, one of the aims of the invention is to provide new AMPs having broad-spectrum antibiotic activity.

The present invention relates to a novel peptide which comprises or consists of SEQ ID NO: 1, with the proviso that the aforesaid peptide does not consist of SEQ ID NOs: 2 to 5.

By the expression "peptide" is meant a contiguous amino acid chain. This contiguous amino acid chain can be called protein if it contains at least 50 amino acids. This contiguous amino acid chain can be either from natural origin or artificial (from chemical synthesis).

By the expression "contiguous amino acid chain" is meant amino acids touching or connected throughout in an unbroken sequence.

Because SEQ ID NO: 1 was issued from *Alvinella pompejana*, it has been called Alvinellacine. The Alvinellacine is the smallest active sequence against microorganisms. This peptide contains 4 cysteines that are involved in Cystine Bridges.

By the word "microorganisms" is meant organisms that are microscopic such as bacteria, fungi, and viruses.

The present invention also relates to a peptide which consists of SEQ ID NO: 6, or derives from SEQ ID NO: 1:
  by modification of its C-terminus, and/or N-terminus, and/or
  by substitution, and/or suppression, and/or addition of one or several amino acids in its peptide chain, and/or
  by modification of at least one —CO—NH— peptide linkage in its peptide chain, particularly by introduction of a retro or retro-inverso type linkage, and/or
  by substitution of at least one amino acid of its peptide chain, with a non-proteinogenic amino acid,
in particular, peptides or fragments of peptides having more than 80%, preferably more than 85%, preferably more than 90% and more preferably more than 95% of homology.

According to the invention, peptide deriving from SEQ ID NO:1 shares at least 80% identity with the amino acids 1 to 22 of SEQ ID NO:1 and have antimicrobial, antiviral and/or fungicide activity.

The SEQ ID NO: 6 corresponds to the prepropeptide of the Alvinellacine.

By the word "prepropeptide" is meant a precursor protein of the Alvinellacine, which includes an N-terminal signal peptide. This prepropeptide is subjected to a posttranslational modification in the Pompeii worm, and thus becomes the active peptide of SEQ ID NO: 1.

By the term "precursor protein" is meant an inactive protein, with no antimicrobial activity.

By the term "antimicrobial activity" is meant an action against bacteria, fungi, and viruses, leading to a decrease of their population and/or leading to the inhibition of microorganism growth.

By the term "signal peptide" is meant a fragment of the amino acid chain of SEQ ID NO: 6, which is a short sequence that directs the transport of said precursor protein in *Alvinella pompejana*. The signal peptide of SEQ ID NO: 6 goes from the $1^{st}$ to the $19^{th}$ amino acid residue.

By the term "posttranslational modification in the Pompeii worm" is meant the deletion process that occurs in *Alvinella pompejana*, corresponding to the cleavage of 186 contiguous amino acids from the N-terminal part of SEQ ID NO: 6, and leading to the obtaining of SEQ ID NO: 1.

By the term "modification of its C-terminus, and/or N-terminus" is meant the replacement of a group, e.g. —COOH or —$NH_2$, located on the first or last amino acid of the peptide of SEQ ID NO: 1, whatever is the aim of the replacement, e.g. to coat the peptide to a support.

By the term "introduction of a retro type linkage" is meant the introduction of a retro amide linkage, which consists of a —NH—CO— peptide linkage in the SEQ ID NO: 1.

By the term "introduction of a retro-inverso type linkage" is meant the introduction of a retro inverso amide linkage, which consists of a —NH—CO— peptide linkage coupled with an inverse absolute configuration of the amino acid.

By the expression "non-proteinogenic amino acids", it must be understood either amino acids not found in proteins (e.g. carnitine, L-canavanine, or L-DOPA), or not coded for in the standard genetic code (e.g. hydroxyproline and selenomethionine).

In an advantageous embodiment, the claimed peptide has at least 80% of identity with peptide of SEQ ID No: 1. Thus, the claimed peptide can have without limitation an amino acid sequence wherein one or more amino acids are substituted or suppressed everywhere inside said sequence or wherein one or more proteinogenic amino acids, i.e. natural amino acids, are added to said sequence, in particular a peptide that contains the four cysteines of SEQ ID NO: 1 which are involved in Cystine Bridges.

The present invention also relates to a peptide as defined above, characterized in that it is isolated and purified from *Alvinella pompejana*.

By the expression "isolated and purified from *Alvinella pompejana*" is meant that the peptide is first extracted from *Alvinella pompejana* and then separated from the other organic debris, e.g. with the intended use of a commercial total protein extraction kit, followed by an affinity chromatography, or other well known technique commonly used by the man skilled in the art.

The present invention also relates to an isolated nucleic acid molecule encoding a peptide as defined above, in particular the nucleic acid molecule of SEQ ID NO: 7, with the proviso that it does not consist of SEQ ID NOs: 8 to 25.

The SEQ ID NO: 7 corresponds to a nucleic acid molecule encoding the above-mentioned prepropeptide of SEQ ID NO: 6.

The SEQ ID NOs: 8 to 25 correspond to disclosed nucleic acid molecules encoding the amino acid chains of SEQ ID NOs: 2 to 5.

By the expression "nucleic acid molecule" is meant a single or double DNA chain, or a single or double RNA chain, including DNA/RNA hybrid, which encode for the claimed peptide.

The present invention also relates to a recombinant nucleic acid construct comprising the above-mentioned nucleic acid molecule operably linked to an expression vector.

By the expression "operably linked" is meant that the aforesaid nucleic acid molecule is linked in a covalent way to an expression vector, permitting ribosome to translate the claimed nucleic acid molecule, or permitting RNA polymerase to produce a mRNA encoding the claimed peptide.

By the term "expression vector" is meant a molecule made of nucleic acids, in particular a plasmid, which comprises a promoter region and optionally an enhancer region. The expression vector can include other genes such as an antibiotic resistance gene, in order to select host cells that contain the nucleic acid molecule encoding the claimed peptide. Recombinant production techniques that use the aforementioned expression vector are well known by a man skilled in the art.

The present invention also relates to a host cell comprising the above-mentioned recombinant nucleic acid construct.

By the term "host cell" is meant any living cell, in particular eukaryotic cell such as fungous cell (e.g. *Aspergillus niger*), but also bacterial cell, or any non-living medium comprising transcriptional and/or translational machinery and optionally organelles from a cell, permitting to amplify the claimed nucleic acid construct and/or produce the claimed peptide.

The present invention further relates to peptides as defined above, for their use as drugs, in particular as antimicrobial, antiviral or fungicide agents.

Another aim of the invention is to provide a composition comprising at least one peptide as defined above.

Still another aim of the invention is to provide a composition as defined above, for its use as an antibacterial agent against Gram-negative and Gram-positive bacteria. A list of Gram – or Gram + bacteria can be found in the DSMZ (Deutsche Sammlung von Mikroorganismen and Zellkulturen) or German Collection of Microorganisms and Cell Cultures catalogue.

Still another aim of the invention is to provide a composition as defined above, for its use in various domains like human and animal healthcare, agriculture and in aquaculture to avoid the development of infectious diseases in farming.

By the term "aquaculture" is meant the farming of aquatic organisms, in particular fish farming, algaculture and integrated multi-trophic aquaculture (IMTA).

By the term "aquatic organisms" is meant any freshwater or saltwater organism, including—without limitation—the following:
  fishes, such as carps, salmons and other cyprinids and salmonids;
  mollusks, such as oysters, clams, cockles, ark shells, scallops and mussels;
  crustaceans, such as crabs, lobsters, shrimps and prawns;
  aquatic plants, such as algae, and phytoplankton.

It is obvious for a man skilled in the art that the claimed peptides could be used in association with other techniques such as vaccines and physical methods intended to reduce the undesired microorganism populations.

The present invention further relates to a pharmaceutical composition comprising at least one of the claimed peptides, in association with a pharmaceutical acceptable vehicle.

By the expression "pharmaceutical acceptable vehicle" is meant any drug carrier chosen by a man skilled in the art.

In this context, they can be use in association with any pharmaceutically acceptable excipient, and in any pharmaceutically acceptable form such as for example caplets, hard gelatin capsules, other caps, soaps and lotions.

In another advantageous embodiment, the claimed pharmaceutical composition further comprise at least one another antimicrobial agent selected in the group comprising:
  tetracyclines, such as oxytetracycline or chlortetracycline;
  quinolones, such as oxolinic acid, flumequine or sarafloxacin;
  sulphonamides, optionally potentiated with trimethoprim or ormethoprim;
  nitrofurans, such as furazolidone;
  macrolides, such as erythromycin or spiramycin (E710);
  florfenicol;
  chloramphenicol.

Another aim of the invention is to provide the above-mentioned pharmaceutical composition for its use in animal and/or human antibiotic therapy.

The optimal administration route (e.g. oral route, topical route, bath treatment) should be determined by a man skilled in the art, as the optimal amount of peptide to use and duration of the treatment.

The present invention also relates to a dietary composition, in particular a food supplement further containing one or more nutritive ingredient, comprising a composition as defined above.

Another aim of the invention is to provide a composition as defined above, wherein said peptides are encapsulated, in particular nanoencapsulated. Encapsulation can bring several benefits, in particular permitting the delivery of the claimed peptides over time. Techniques for encapsulation and nanoencapsulation are well known by a man skilled in the art.

Still another aim of the present invention is to provide a disinfectant comprising a composition containing at least one of the claimed peptide.

By the term "disinfectant" is meant a mixture of compounds that provides an antimicrobial, antiviral and/or fungicide activity, and which is used for this purpose.

Amongst the other possible applications, it should be noted that the claimed peptides could be used for example in growth media, in particular media for insect and eukaryotic cells, in order to prevent the contamination of these media by microorganisms.

Figure 2:
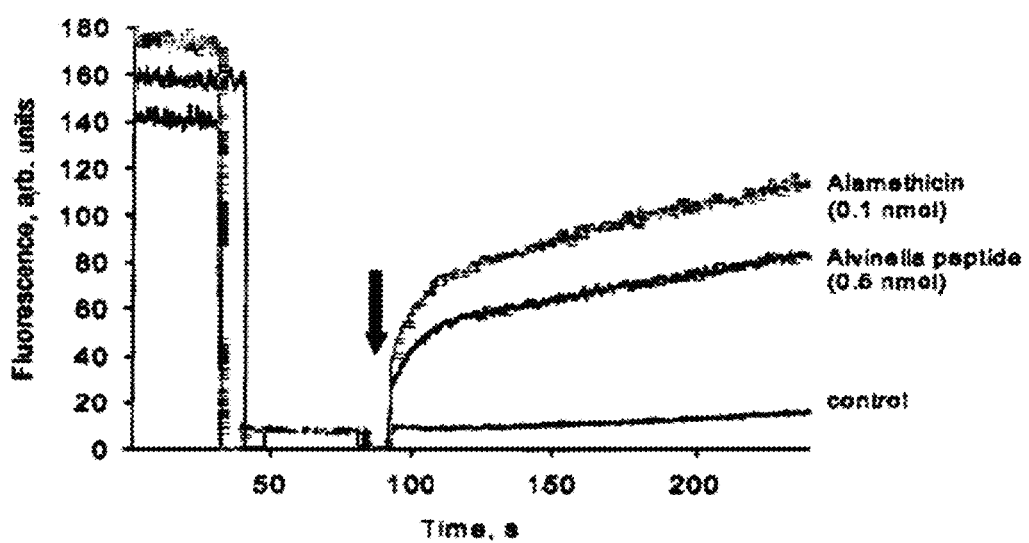
Figure 3:
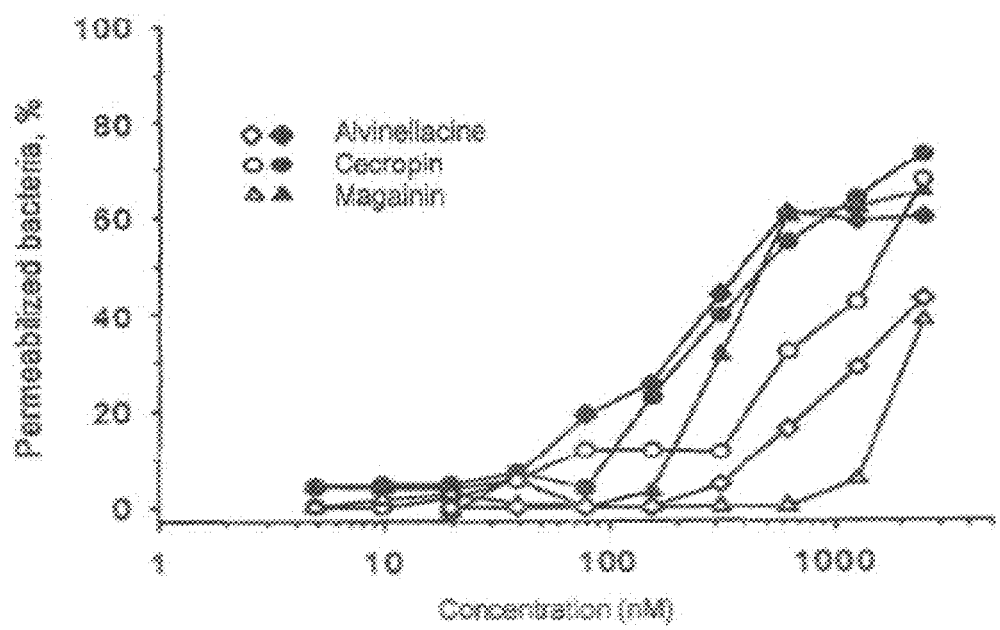

The following examples 1 to 3 and FIGS. 1 to 3 illustrate the invention.

FIG. 1 presents the chromatographic profile of the extract from *Alvinella pompejana*, obtained after its pre-purification on a Sep-Pak® 20 g column (Waters™) and its purification by reversed-phase chromatography (RP-HPLC) using a C18 250×4.1 mm column (218TP54 Vydac™), as described in the experimental part. The two thicker lines indicate fractions that possess antimicrobial properties.

x-axis from left to right: Elution time (min);
y-axis (left side): optical density (O.D.) at 255 nm;
y-axis (right side): percentage of ACN in the eluant.

FIG. 2 presents the ability of the Alvinellacine to create pores in liposomes, herein used to mimic bacterial membranes.

x-axis from left to right: time (s);
y-axis (left side): fluorescence (arbitrary units).

The arrow shows the moment of addition of Alamethicin and the Alvinellacine.

The negative control shows the background noise, corresponding to the fluorescence measured without permeabilization of liposomes.

FIG. 3 presents the permeabilization of Gram-positive bacteria (*Bacillus megaterium*) and Gram-negative bacteria (*Escherichia coli*) after intended use of the Alvinellacine and two other AMPs (Cecropin originated from pork and Magainin originated from amphibian). These experiences were carried out at pH 7.4. The permeabilization of bacteria was measured 10 minutes after addition of each AMP for *B. megaterium*, while the same measurement was done after 120 minutes after addition of each AMP for *E. coli*.

x-axis from left to right: concentration of Alvinellacine, Cecropin and Magainin (nM);
y-axis (left side): permeabilized bacteria (%).

Black symbols are for *E. coli* and white symbols are for *B. megaterium*.

EXAMPLE 1

Extraction, Purification and Sequencing of the Endogenous Alvinellacine from *Alvinella pompejana*

20 entire full-grown and sexually mature Pompeii worms were collected on the East Pacific Rise, by 3,000 meters deep. These adult worms were crushed, and the homogeneous resulting mixture was acidified to pH 3 by addition of HCl 1M. Then the solution was centrifuged at 10,000 g during 30 minutes. Proteins were thus concentrated in the centrifugation pellet and eliminated.

The supernatant containing the peptides was pre-purified on a pre-packed-with-methanol Sep-Pak® 20 g column (Waters™), thereafter washed with HPLC grade water which was pre-acidified with a 0.05% trifluoroacetic acid (TFA) solution. Elution was carried out with a 2 to 60% gradient of acetonitrile (ACN), which was pre-acidified with a 0.05% trifluoroacetic acid (TFA) solution.

The fraction obtained with the 60% ACN eluant was then purified by reversed-phase chromatography (RP-HPLC) using a C18 250×4.1 mm column (218TP54 Vydac™). A 2 to 62% gradient of ACN was used for this purification. The optical density of each collected fraction was subsequently measured, in order to obtain a chromatographic profile (FIG. 1). Each peak on the chromatographic profile corresponds to a fraction that was dried, re-suspended in purified water and then tested for its antimicrobial activity.

The active fractions were further purified by successive RP-HPLCs using a C18 250×2.1 mm column (218TP52 Vydac™). The purity degree and the molecular mass of the active peptides were estimated by mass spectrometry.

The purified peptides were sequenced by Edman degradation (a well known technique for a man skilled in the art). The results show that one obtained sequence corresponds to an active peptide of SEQ ID NO: 1 that was totally unknown. Because of its origin, this peptide has been called Alvinellacine. The use of classical reverse genetics techniques permitted to obtain a nucleic acid molecule encoding the precursor protein of this peptide. The precursor protein of SEQ ID NO: 6 includes a signal peptide that goes from the $1^{st}$ to the $19^{th}$ amino acid residue of the sequence. The complementary DNA encoding the prepropeptide was further deduced from it and consists of SEQ ID NO: 7.

EXAMPLE 2

Evaluation of Mechanism of Antibacterial Activity

The mechanism of antibacterial activity was determined using liposomes filled with a fluorescent reagent. Liposomes consist of a bi-layer of phospholipids herein used to mimic the bacterial membrane. Permeabilization of the liposomes would result in a release of the internal compound, thus reacting with the medium and producing a fluorescent light that can be measured by spectrometry. The test is carried out with both negative and positive controls. Alamethicin, which is an antibiotic known to create pores in the bacterial membrane, is used as the positive control. The negative control is a solution of liposomes, intended for measurement of background noise (FIG. 2).

Results show that the Alvinellacine acts as the Alamethicin and permealibilizes the bi-layer of phospholipids.

This mode of action would not favour the emergent evolution of antibiotic-resistant strains.

EXAMPLE 3

Evaluation of Antibacterial Activity and Comparison with Other AMPs

The minimal inhibitory concentration (MIC) was determined according to the method of Hancock (Hancock, R. E. W. Sep. 19, 1999, posting date. [Online.] Hancock Laboratory Methods. Department of Microbiology and Immunology, University of British Columbia, British Columbia, Canada. [Antibiotics and Antimicrobial Peptides: MIC Determination by Microtitre Broth Dilution Method, last accessed September $21^{st}$.]). Permeabilization of bacterial membranes and pore-forming activity were assayed as previously described (Herbst, R., Ott, C., Jacobs, T., Marti, T., Marciano-Cabral, F., Leippe, M. Pore-forming polypeptides of the pathogenic protozoon *Naegleria fowleri*. J. Biol. Chem. 2002. 277:22353-22360).

In liquid growth inhibition assay, the purified Alvinellacine was very active against the human pathogen *Staphylococcus aureus* (MIC 0.385-0.75 µM) and the clam pathogen *Vibrio alginolyticus* (MIC 0.006-0.012 µM).

To investigate the mode of action of Alvinellacine, we used the fluorescent dye SYTOX-Green® and either the Gram-positive *Bacillus megaterium* or the Gram-negative *E. coli* (FIG. 3). Results of this assay demonstrate that Alvinellacine rapidly permeabilizes bacterial membranes and is potently active against Gram-negatives and in a lesser extent against Gram-positives. Within the measurement period, the activity of Alvinellacine against the Gram-negative bacterium tested appeared to be over one order of magnitude higher than those for the well-known antimicrobial peptides Cecropin P1 and Magainin II. A lower activity was detected against the Gram-positive bacteria compared to the two positive controls. We also measured the pore-forming activity of Alvinellacine to further characterize its mode of action by using a minimalistic membrane system. More precisely, we monitored the dissipation of a membrane potential induced in liposomes composed of azolectin, a crude phospho lipid mixture from soy bean. Pore-forming activity was detected at final concentrations up to 0.5 nM, whereas the positive control Alamethicine gave a signal at 0.1 nM.

---

The invention claimed is:

1. A peptide consisting of SEQ ID NO: 1, said peptide having antibacterial activity, wherein said peptide is an isolated and purified peptide from *Alvinella pompejana*.

2. A method for treating gram-negative, gram-positive bacterial infections, comprising administering an effective amount of the peptide according to claim 1, to a patient in need thereof, wherein the bacterial infection is caused by a bacteria selected from the group consisting of Gram-negative bacteria, Gram-positive bacteria and combinations thereof.

3. A composition comprising said peptide according to claim 1.

4. A method for treating gram-negative, gram-positive bacterial infections, comprising administering an effective amount of the composition according to claim 3, to a patient in need thereof, wherein the bacterial infection is caused by a bacteria selected from the group consisting of Gram-negative bacteria, Gram-positive bacteria and combinations thereof.

5. A pharmaceutical composition comprising said peptide according to claim 1 and a pharmaceutically acceptable vehicle.

6. The pharmaceutical composition according to claim 5, further comprising at least one other antimicrobial agent selected from the group consisting of:
tetracyclines;
quinolones;
sulphonamides;
nitrofurans;
macrolides;
florfenicol; and
chloramphenicol.

7. A method for treating gram-negative, gram-positive bacterial infections, comprising administering an effective amount of the pharmaceutical composition according to claim 6, to a patient in need thereof, wherein the bacterial infection is caused by a bacteria selected from the group consisting of Gram-negative and Gram-positive.

8. A dietary composition comprising a composition according to claim 3; and one or more nutritive ingredients.

9. The composition according to claim 3, wherein said peptide is encapsulated.

10. A disinfectant comprising a composition according to claim 3.

* * * * *